US007763286B2

(12) United States Patent
Lee et al.

(10) Patent No.: US 7,763,286 B2
(45) Date of Patent: Jul. 27, 2010

(54) **COMPOSITION COMPRISING AN EXTRACT OF *TIARELLA POLYPHYLLA* AND TIARELLIC ACID ISOLATED THEREFROM HAVING ANTIINFLAMMATORY, ANTIALLERGIC AND ANTIASTHMATIC ACTIVITY**

(75) Inventors: Hyeong Kyu Lee, Daejeon (KR); Sei Ryang Oh, Daejeon (KR); Kyung Seop Ahn, Daejeon (KR); Joong Ku Lee, Daejeon (KR); Sang Ku Lee, Daejeon (KR); Jung Hee Kim, Daejeon (KR); Doo Young Kim, Daejeon (KR); Gui Hua Quan, Daejeon (KR); Ok Kyoung Kwon, Daejeon (KR); Eun Ah Kim, Naju-si (KR); Soon Ja Choi, Daejeon (KR); Guang Hai Shen, Daejeon (KR); Mi Jin Kim, Daejeon (KR); Bo Young Park, Daejeon (KR); Byung Sun Min, Daejeon (KR); Gyoon Hee Han, Hwaseong-si (KR); Hea Young Park, Seoul (KR); Gun Cheol Kim, Daejeon (KR); Joo Heon Kim, Daejeon (KR); So Young Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 58 days.

(21) Appl. No.: 11/989,053

(22) PCT Filed: Jul. 18, 2006

(86) PCT No.: PCT/KR2006/002807

§ 371 (c)(1),
(2), (4) Date: Jan. 18, 2008

(87) PCT Pub. No.: WO2007/011148

PCT Pub. Date: Jan. 25, 2007

(65) Prior Publication Data

US 2009/0148542 A1 Jun. 11, 2009

(30) Foreign Application Priority Data

| Jul. 18, 2005 | (KR) | 10-2005-0064668 |
| Jul. 18, 2005 | (KR) | 10-2005-0064669 |
| Jul. 18, 2006 | (KR) | 10-2006-0066861 |
| Jul. 18, 2006 | (KR) | 10-2006-0066866 |

(51) Int. Cl.
*A61K 36/00* (2006.01)
*A61K 47/00* (2006.01)

(52) U.S. Cl. ........... 424/725; 514/826; 514/783; 424/439

(58) Field of Classification Search ............. None
See application file for complete search history.

(56) References Cited

FOREIGN PATENT DOCUMENTS

| EP | 1213027 | 6/2002 |
| KR | 10-2003-0042123 A | 5/2003 |
| KR | 2003042123 A * | 5/2003 |
| WO | WO 02-102396 A1 | 12/2002 |

OTHER PUBLICATIONS

Allergy reaction induction from Merck Manual, accessed on Jun. 8, 2009, pp. 1-6.*
Asthma from Merck manual, pp. 1-11, accessed on Jul. 21, 2009.*
Valenta et al, Component-resolved diagnosis to optimize allergen-specific immunotherapy in the Mediterranean area, Journal of Investigational Allergology and Clinical Immunology, (2007) vol. 17, No. Suppl. 1, pp. 36-40) teach allergen-specific immunotherapy (SIT).*
Asero, Plant food allergies: A suggested approach to allergen-resolved diagnosis in the clinical practice by identifying easily available sensitization markers, International Archives of Allergy and Immunology, (2005) vol. 138, No. 1, pp. 1-11.*
Rachelefsky, Improving patient adherence: The asthma template, Pediatric Asthma Allergy & Immunology, (FAL 2007) vol. 20, No. 3, pp. 146-156.*
van Schayck Onno et al, Is there any role for allergen avoidance in the primary prevention of childhood asthma, The Journal of allergy and clinical immunology, (Jun. 2007) vol. 119, No. 6, pp. 1323-1328.*
Wild et al, Immunotherapy for food allergy, Current allergy reports, (Jan. 2001) vol. 1, No. 1, pp. 48-53.*
Zahra et al, Wheat anaphylaxis in children, Immunological investigations, (2007) vol. 36, No. 2, pp. 175-182.*
Singh, Management of acute asthma, Indian Journal of Pediatrics, (Sep. 2001) vol. 68, No. Suppl. 4, pp. S23-S30) teaches Hospitalization due to acute severe asthma represents a failure in the preventive, long-term as well as home care of asthma.*
Park, S.H., et al. "Anticomplement activities of oleanolic acid monodesmosides and bisdesmosides isolated from *Tiarella polyphylla*." *Arch. Pharm. Res.* 1999, V. 22, No. 4, pp. 428-431. (abstract).
Moon, H.I. et al. "Triterpenoid from *Tiarella polyphylla*, regulation of type 1 procollagen and MMP-1 in ultraviolet irradiation of cultured old age dermal fibroblasts." *Arch. Pharm. Res.* 2004, V. 27, No. 10, pp. 1060-1064. (abstract).

(Continued)

*Primary Examiner*—Qiuwen Mi
(74) *Attorney, Agent, or Firm*—Ohlandt, Greeley, Ruggiero & Perle, L.L.P (57) ABSTRACT

The present invention relates to a composition comprising an extract of *Tiarella polyphylla*, and tiarellic acid isolated therefrom having anti-inflammatory, anti-allergic and anti-asthmatic activity. The extract of *Tiarella polyphylla* and the tiarellic acid isolated therefrom shows the inhibitory effect on the $LTC_4$ release in vitro test and the suppressive effect on the IgE level and the cytokine (IL-4, IL-5 and IL-13) production, airway hyperresponsiveness, and leukocyte infiltration in OVA-induced asthmatic mice. Therefore, it can be used as the therapeutics or functional health food for treating and preventing inflammatory, allergic and asthmatic disease.

2 Claims, 1 Drawing Sheet

OTHER PUBLICATIONS

Park, S.H., et al. "Structure determination of a a new lupane-type tritepene, tiarellic acid, isolated from *Tiarella polyphylla*." *Arch. Pharm. Res.* 2002, v. 25, No. 1, pp. 57-60. (abstract).

Kumar, R.K. *Pharmacol. Ther.,* 91, pp. 93-104, 2001. (abstract).

Elias, JA, et al., *J Clin Invest.,* 111, pp. 291-297, 2003. (abstract).

Moffat JD., *Pharmacol Ther.,* 107, pp. 343-357, 2005. (abstract).

Spina, D., et al., *Trends Pharmacol Sci,* 23, pp. 311-315, 2002. (abstract).

Bochner, B.S. et al., *Annu. Rev. Immunol.,* 12, pp. 295-335, 1994. (abstract).

Bousquet, J. et al., *N. Engl. J. Med.,* 323, pp. 1033-1039, 1990. (abstract).

Riffo-Vasquez, Y., et al., *Pharmacol Ther.,* 94, pp. 185-211, 2002. (abstract).

Baatjes, A.J., et al., *Pharmacol. Ther.,* 95, pp. 63-72, 2002 (abstract).

Wang, Z., et al., *Biol. Pharm. Bull.,* 24, pp. 159-162, 2001. (abstract).

Lee, S.H., et al., *Biol. Pharm. Bull.,* 27, pp. 786-788, 2004. (abstract).

OCP3000; Allmedicus, Korea. Hamelmann, E. et al.,*Am J Respir Crit Care Med.,* 156, pp. 766-775, 1997. (abstract).

Myou, S., et al., *J. Exp. Med.,* 198, pp. 1573-1582, 2003. (abstract).

International Search Report dated Sep. 18, 2006 based on corresponding Patent Application Serial No. PCT/KR2006/002807.

Moffatt, James D. "*What targets have knockouts revealed in asthma?*", Pharmacology & Therapeutics 107 (2005) pp. 343-357.

Baatjes et al. "*Anti-allergic therapies: effects on eosinophil progenitors*", Pharmacology & Therapeutics 95 (2002) pp. 63-72.

Kumar, Rakesh K. "*Understanding airway wall remodeling in asthma: a basis for improvements in therapy?*" Pharmacology & Therapeutics 91 (2001) pp. 93-104.

Bochner et al. "*Immunological Aspects of Allergic Asthma*," Immunology of Asthma, 1994, pp. 295-327.

Park et al. "*Structure Determination of a New Lupane-type Triterpene, Tiarellic Acid, Isolated from Tiarella polyphylla,*" Archives of Pharmacal Research, vol. 25, No. 1, Jan. 8, 2002, pp. 57-60.

Spina et al. "*Asthma—a need for a rethink?*" Trends in Pharmacological Sciences, vol. 23, No. 7, Jul. 2002, pp. 311-315.

Bousquet et al. "*Eosinophilic Inflammation in Asthma,*" The New England Journal of Medicine, vol. 323, No. 15, pp. 1033-1039., 1990.

Vasquez et al. "*Role of cytokines and chemokines in bronchial hyperresponsiveness and airway inflammation*", Pharmacology & Therapeutics 94 (2002) pp. 185-211.

\* cited by examiner

COMPOSITION COMPRISING AN EXTRACT OF TIARELLA POLYPHYLLA AND TIARELLIC ACID ISOLATED THEREFROM HAVING ANTIINFLAMMATORY, ANTIALLERGIC AND ANTIASTHMATIC ACTIVITY

TECHNICAL FIELD

The present invention relates to a composition comprising an extract of Tiarella polyphylla and tiarellic acid isolated therefrom having anti-inflammatory, anti-allergic and anti-asthmatic activity.

BACKGROUND ART

Asthma has been regarded as a complex syndrome occurring in the airways, which shows various disorders such as airflow obstruction, acute or chronic inflammation, airway hyper-responsiveness (AHR) and structural remodeling (Kumar R. K. Pharmacol. Ther., 91, pp 93-104, 2001).

Allergic inflammation occurring in the airways has been reported to play a critical role in asthma development and the number of patients suffering from allergic asthma has been increased to about 10% of the population in the world recently. It has been reported that the number has been reached to seventeen million in America and the market scale of the medication for allergic asthma has been enlarged to 640 billion $ in America till now.

Asthma can be classified into two types, i.e., extrinsic asthma and intrinsic asthma. Extrinsic asthma caused by the exposure of antigen such as house dust mite *Dermatophagoides* as a main antigen, pollen, epithelium of animal, fungi etc shows positive reaction in skin test or bronchial provocation test against the antigen, and generally occurs in younger people. Intrinsic asthma caused by upper respiratory infection, exercise, emotional instability, cold weather, the change of humidity occurs in adult patients.

According to the aspect of pathophysiology, asthma has been recognized as a chronic inflammation occurred by following procedure; Inflammatory cells are proliferated, differentiated, and activated caused by cytokines reproducing in T-helper 2 immune cells and is moved to air way or neighboring tissue thereof. The activated inflammatory cells such as neutrophil, mast cell etc release a variety of inflammatory mediators, such as cytokines, chemokines, signaling molecules, adhesion molecules and growth factors and the structural cells in airways are involved in various stages of asthma (Elias J A et al., J Clin Invest., 111, pp 291-7, 2003). In numerous studies using knockout mice models and clinical research, the critical observations in asthma could fall into several characteristic parameters, such as immune responses, eosinophilia, AHR and structural remodeling (Moffatt J D. Pharmacol Ther, 107, pp 343-57, 2005; Spina D et al., Trends Pharmacol Sci, 23, pp 311-5, 2002). Each of the parameters seems not to have direct correlations with one another; however, IgE-mediated immune response and eosinophilia are prominent symptoms in the airways of allergic asthma (Bochner B. S. et al., Annu. Rev. Immunol., 12, pp 295-335, 1994; Bousquet J et al., N. Engl. J. Med., 323, pp 1033-9, 1990), and the produced cytokines such as IL-4, IL-5 and IL-13 in the allergic process also play an important role in AHR development and airway remodeling (Riffo-Vasquez Y et al., Pharmacol. Ther., 94, pp 185-211, 2002). Indeed, asthma is a result of orchestrated inflammatory events, many of which involve specific inhibitors acting on the pathway of asthma, for example, histamine H1 antagonists, thromboxane antagonists, platelet-activating-factor antagonists, cyclooxygenase inhibitors, nitrogen monooxygenase inhibitors and prostaglandin inhibitors, have been tried but have failed in clinical trials (Moffatt J. D., Pharmacol. Ther., 107, pp 343-57, 2005). In contrast, glucocorticoids, which suppress the progenitor levels of inflammatory cells to baseline by widespread inhibition of cytokine synthesis and cytokine mediated immune-cell survival, has been used to manage the symptoms of asthmatic patients over a period of 30 years as far (Baatjes A. J. et al., Pharmacol, Ther., 95, pp 63-72, 2002). These reports suggest that the therapeutic approach for asthma management should focus on restoring the balance of asthmatic parameters rather than searching for potent inhibitors of specific pathways of the asthmatic process.

Tiarella polyphylla D. Don (Saxifragaceae) is a single species belonged to the genus in Korea. It inhabits in South-West in China but only on the summit of Ullung Island in Korea. Previously, it has been isolated tiarellic acid with corosolic acid, tormentic acid and so on (Park et al., Arch Pharm Res., 25, pp 57-60, 2002), and others reported an inhibitory effect on the expression of MMP-1 and type 1 procollagen in UV-irradiated skin fibroblasts (Moon et al., J Ethnopharmacol., 98, pp 185-189, 2005).

However, there has been not reported or disclosed about the suppressive effect on inflammatory, allergic and asthmatic disease of the extract of Tiarella polyphylla and tiarellic acid isolated therefrom in any of above cited literatures, the disclosures of which are incorporated herein by reference.

Accordingly, the present inventors have discovered that the extract of Tiarella polyphylla and tiarellic acid isolated therefrom show the inhibitory effect of tiarellic acid against $LTC_4$ release in vitro and the suppressive effect on the IgE level and the cytokine (IL-4, IL-5 and IL-13) production, airway hyper-responsiveness, and leukocyte infiltration in OVA-induced asthmatic mice for the expectiation of contribution to asthma management.

DISCLOSURE OF INVENTION

Technical Problem

Accordingly, there have been still needed to discover more effective drug to treat and prevent inflammatory, allergic and asthmatic disease without toxicity till now.

Technical Solution

Accordingly, it is an object of the present invention to provide a composition comprising a crude extract or organic solvent soluble extract of T. polyphylla, as an active ingredient for the treatment and prevention of inflammatory, allergic and asthmatic disease.

The term "crude extract" disclosed herein comprises the extract prepared by extracting plant material with water, $C_1$-$C_4$ lower alcohols such as methanol, ethanol, preferably methanol and the like, or the mixtures thereof.

The term "organic solvent soluble extract" disclosed herein can be prepared by extracting the above described crude extract with organic solvent, for example, butanol, acetone, ethyl acetate, chloroform, dichloromethane or hexane, preferably butanol.

The present invention provides a pharmaceutical composition comprising tiarellic acid isolated from a crude extract or organic solvent soluble extract of T. polyphylla, represented by following chemical formula (I), or a pharmaceutically acceptable salt thereof as an active ingredient in an effective amount to treat and prevent inflammatory, allergic and asthma disease.

(I)

In accordance with another aspect of the present invention, there is also provided a use of crude extract or organic solvent soluble extract of *T. polyphylla*, or tiarellic acid isolated therefrom for manufacture of medicines employed for treating or preventing inflammatory, allergic and asthmatic disease.

In accordance with another aspect of the present invention, there is also provided a method of treating or preventing inflammatory, allergic and asthmatic disease in mammals, wherein the method comprises administering a therapeutically effective amount of crude extract or organic solvent soluble extract of *T. polyphylla*, or tiarellic acid isolated therefrom into the mammal suffering with inflammatory, allergic and asthmatic disease.

An inventive extract isolated from *T. polyphylla*, and tiarellic acid isolated therefrom may be prepared in accordance with the following preferred embodiment.

Hereinafter, the present invention is described in detail.

For the present invention, for example, the dried whole plant of *T. polyphylla* is cut into small pieces and the piece was mixed with 2 to 20-fold, preferably, 5 to 10-fold volume of polar solvent, for example, water, $C_1$-$C_4$ lower alcohol such as methanol, ethanol, butanol, or the mixtures thereof, preferably methanol; and was heated at the temperature ranging from 20 to 100° C., preferably from 20 to 50° C., for the period ranging 10 to 48 hours, preferably 20 to 30 hours, by reflux extraction with hot water, cold water extraction, ultrasonication or conventional extraction, preferably by cold water extraction; the residue was filtered and then the filtrate is dried to obtain polar solvent soluble extract thereof.

In the above crude extract prepared by above step, is suspended in water, and then is mixed with 1 to 100-fold, preferably, 1 to 5-fold volume of organic solvent butanol, acetone, ethyl acetate, chloroform, dichloromethane or hexane, preferably butanol to obtain organic solvent soluble extract of the present invention.

The above organic solvent soluble extract is further subjected to silica gel column chromatography (70-230 mesh, 8.5×65 cm) filled with silica gel eluting with mixture solvent of n-hexane:ethyl acetate (ethyl acetate 10-20%, step gradient), and a chloroform:methanol (methanol 0-100%, step gradient) to obtain 9 fractions. Among the fractions, the 6 fraction is further subjected to repeated silica gel column chromatography using a normal phase silica column (silica gel, 230-400 mesh, 6.0×60 cm, chloroform-methanol mixture, methanol 5-50% step gradient) to obtain the tiarellic acid of the present invention. The structure was confirmed by NMR ($^1$H, $^{13}$C, DEPT, HMQC, HMBC), EI-MS and optical rotation with those reported previously (Park et al., *Arch Pharm Res.*, 25, pp 57-60, 2002), and the purity was analyzed as more than 99.5% by HPLC system (Shimadzu SCL-10A woth SPD-M 10A vp PDA detector, column; phenomenex Synergi 4 um Fusion RP-80, 4.6×150 nm, elution: ACN/0.1% TFA in DW, 4/1, v/v).

In accordance with another aspect of the present invention, there is provided a pharmaceutical composition comprising a crude extract and organic solvent soluble extract of *T. polyphylla* or tiarellic acid isolated therefrom prepared by the above described preparation method for the treatment and prevention of inflammatory, allergic and asthmatic disease as active ingredients.

In accordance with another aspect of the present invention, there is also provided a use of a crude extract and organic solvent soluble extract of *T. polyphylla* or tiarellic acid isolated therefrom prepared by the above described preparation method for manufacture of medicines employed for treating or preventing inflammatory, allergic and asthmatic disease.

In accordance with another aspect of the present invention, there is also provided a method of treating or preventing inflammatory, allergic and asthmatic disease, wherein the method comprises administering a therapeutically effective amount of comprising a crude extract and organic solvent soluble extract of *T. polyphylla* or tiarellic acid isolated therefrom prepared by the above describe preparation method.

The inventive compound represented by chemical formula (I) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluenesulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the present compound comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate (mesylate) salt and p-toluenesulfonate (tosylate) salt etc, which can be prepared by the conventional method well known in the art.

The inventive composition for treating and preventing inflammatory, allergic and asthmatic disease may comprises the above described extracts or compounds as 0.1~50% by weight based on the total weight of the composition.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or compound varies depending on the condition and the weight of the subject, severity, drug form, route and period of administration, and may be chosen by those skilled in the art. However, in order to obtain desirable effects, it is generally recommended to administer at the amount ranging from 0.0001 to 100 mg/kg, preferably, 0.001 to 10 mg/kg by weight/day of the inventive extract of the present invention. The dose may be administered in single or divided into several times per day.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

It is the other object of the present invention to provide a functional health food comprising the extract or compounds isolated from *T. polyphylla* together with a sitologically acceptable additive for the prevention and alleviation of inflammatory, allergic and asthmatic disease.

To develop for functional health food, examples of addable food comprising the above extracts or compounds of the present invention are various food, beverage, gum, vitamin complex, health improving food and the like, and can be used as powder, granule, tablet, chewing tablet, capsule or beverage etc.

The above described composition therein can be added to food, additive or beverage, wherein the amount of the above described extract or compound in food or beverage may generally range from about 0.01 to 80 w/w %, preferably 0.01 to 15 w/w % of total weight of food for the health food composition and 0.02 to 5 g, preferably 0.3 to 1 g on the ratio of 100 ml of the health beverage composition.

Providing that the health beverage composition of present invention contains the above described extract or compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100□ of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

Inventive extract of the present invention has no toxicity and adverse effect therefore they can be used with safe.

The present invention is more specifically explained by the following examples. However, it should be understood that the present invention is not limited to these examples in any manner.

ADVANTAGEOUS EFFECTS

The present invention provides a pharmaceutical composition and a health food comprising an extract of *T. polyphylla* or tiarellic acid isolated therefrom as an active ingredient in an effective amount to treat and prevent inflammatory, allergic and asthmatic disease.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

MODE FOR THE INVENTION

The present invention is more specifically explained by the following examples. However, it should be understood that the present invention is not limited to these examples in any manner.

The following Reference Example, Examples and Experimental Examples are intended to further illustrate the present invention without limiting its scope.

Example 1

Preparation of the Crude Extract of *T. polyphylla*

*T. polyphylla* was collected in August 2003, Ullung Island, Korea and the voucher specimen (PEB 3068) was deposited in the Plant Extract Bank of Korea Research Institute of Bioscience and Biotechnology, KRIBB) located in Daejeon, Korea.

1.1 kg of dried *T. polyphylla* was cut into small pieces, mixed with 5 L of methanol and the mixture was stirred at room temperature for 24 hours, extracted with cold water at three times. The extract was filtered with filter paper to remove the debris. The filtrate was pooled and concentrated by rotary evaporator 55~65° C. under reduced pressure and dried with freezing dryer to obtain 100.5 g of dried crude extract of *T. polyphylla*.

Example 2

Preparation of Butanol Soluble Fraction

1 L of distilled water was added to 100.5 g of the crude extract obtained in Example 1. 1 L of butanol was added thereto in separatory funnel and shaken vigorously to divide into butanol soluble layer and water soluble layer.

Above butanol soluble layer was concentrated with rotary evaporator, dried with freeze dryer to obtain butanol soluble extract, and finally, 80.0 g of butanol soluble extract and water soluble extract were obtained, to use as a sample in the following experiments.

Example 3

Preparation of Tiarellic Acid from the Extract of *T. polyphylla*

3.29 kg of the dried whole plants of *T. polyphylla* extracted with methanol (10 L) twice at room temperature to obtain 352 g of an extract. This extract was suspended in 1 L of water and partitioned with an equal volume of n-hexane. 65.1 g of the n-hexane soluble fraction was then subjected to a silica gel column chromatography (70-230 mesh, 8.5×65 cm) and eluted with a n-hexane-ethyl acetate mixture (ethyl acetate 10-20%, step gradient), and a chloroform-methanol mixture (methanol 0-100%, step gradient), successively, and yielded 9 fractions (Fr. 1-Fr. 9). 7.4 g of the Fr. 6 (between chloroform-methanol 9/1-7/3, v/v) was subjected to column chromatography using a normal phase silica column (silica gel, 230-400 mesh, 6.0×60 cm, chloroform-methanol mixture, methanol 5-50% step gradient) to yield 400 mg of tiarellic acid. The structure was confirmed by NMR ($^1$H, $^{13}$C, DEPT, HMQC, HMBC), EI-MS and optical rotation with those reported previously (Park et al., *Arch Pharm Res.*, 25, pp 57-60, 2002) and the purity more than 99.5% was analyzed by HPLC system (Shimadzu SCL-10A with SPD-M 10A vp PDA detector, column; Phenomenex Synergi 4 um Fusion RP-80, 4.6×50 mm, elution: ACN/0.1% TFA in DW, 4/1, v/v).

Tiarellic Acid

Needles (MeOH);

mp 254-256° C.;

$[a]2$ 3 D+94 (pyridine, c 0.14);

IR (KBr, cm$^{-1}$): 3491 (OH), 1689 (CO), 1645 (C=C), 1450, 1388, 1262, 1222, 1044; HRMS m/z 472.3552 (M$^+$, Calcd for $C_{30}H_{48}O_4$: 472.3553);

EIMS (rel. int.) m/z: 472 [M]$^+$ (61), 454 [M-H$_2$O]$^+$ (34), 436 [M-2H$_2$]$^+$ (62), 424 (42), 396 (26), 205 (75), 187 (71), 175 (87), 173 (100);

$^{13}$C-NMR (150 MHz, pyridine-d$_5$): 13.0 (C-24), 17.4 (C-25), 17.5 (C-26), 18.7 (C-6), 18.8 (C-28), 19.4 (C-30), 21.3 (C-11), 25.8 (C-15), 26.7 (C-12), 27.9 (C-2), 30.1 (C-21), 37.7 (C-10), 38.2 (C-7), 38.3 (C-16), 39.2 (C-1), 39.6 (C-13), 40.4 (C-22), 40.8 (C-8), 42.9 (C-4), 43.0 (C-17), 48.1 (C-19), 49.2 (C-5), 51.4 (C-18), 51.6 (C-9), 60.4 (C-14), 68.2 (C-23), 73.6 (C-3), 110.2 (C-29), 150.9 (C-20), 178.3 (C-27).

$^1$H-NMR (600 MHz, pyridine-d5): 1.05, 1.71 (2H, m, each, H-1), 1.82, 1.91 (2H, m, each, H-2), 4.02 (1H, dd, J=4.7, 11.6 Hz, H-3), 1.51 (1H, dd, J=1.5, 12.0 Hz, H-5), 1.48, 1.65 (2H, m, each, H-6), 1.87, 2.06 (2H, m, each, H-7), 2.02 (1H, dd, J=1.7, 12.7 Hz, H-9), 1.32, 1.64 (2H, m, each, H-11), 1.87, 2.60 (2H, m, each, H-12), 1.88 (1H, m, H-13), 1.67, 2.28 (2H, m, each, H-15), 1.70, 1.78 (2H, m, each, H-16), 1.81 (1H, m, H-18), 2.60 (1H, m, H-19), 1.36, 1.97 (2H, m, each, H-21), 1.16, 1.40 (2H, m, each, H-22), 3.57, 4.07 (2H, d, J=10.4, each, H-23), 1.04 (3H, s, H-24), 1.01 (3H, s, H-25), 1.21 (3H, s, H-26), 0.90 (1H, s, H-28). 4.76, 4.96 (2H, s, each, H-29), 1.86 (3H, d, J=6.4 Hz, H-30), Experimental Example 1

Animal Sensitization and Airway Challenge

Groups of mice (n=5-6) were studied; they received the following treatment: (1) sham-sensitization plus challenge with phosphate-buffered saline (PBS; ipNeb); (2) sensitization plus challenge with OVA (ovalbumin: Sigma A5503; Sigma, St. Louis, Mo.) (ipNeb); (3) sensitization with OVA (ip) plus challenge with OVA (Neb) and samples (tiarellic acid or zileuton, po). Briefly, mice were sensitized with intraperitoneal injection of 20 μg OVA, which was emulsified with 2 mg of aluminum hydroxide in 100 μl of PBS buffer (pH 7.4) on days 0 and 11. The mice were challenged through the airways with OVA (1% in PBS) for 20 min using an ultrasonic nubuilizer (NE-U12; Omron Corp., Tokyo, Japan) on days 19, 20, 21 and 25 after the initial sensitization. The mice were sacrificed 48 hours after the last challenge (day 27) to determine the suppressive effect of extract of *T. polyphylla* and tiarellic acid on the airways of allergic asthma.

Experimental Example 2

MTT Assay

To investigate the cytotoxic activity of inventive extract of *T. polyphylla* and tiarellic acid isolated therefrom, (3-[4,5-dimethylthiazol-2-yl]-2,5-diphenyl tetrazolium bromide (MTT) assay method was performed by following procedure (Wang Z et al., *Biol., Pharm. Bull.*, 24, pp 159-162, 2001).

Promyelotic HL-60 cells (HL-18103, $5 \times 10^5$ cells/ml) were seeded on 96-well plates under NGF-free condition. After 24 hours incubation, the cells were treated with the mixture of samples dissolved in 10 µl of DMSO and 10 µl of MTT solution (5 mg/ml), and incubated for 4 hours under the similar condition. 4 hours later, MTT was removed and 100 µl of DMSO was dropped into each well to dissolve crystals. UV absorbance was measured by microplate reader (BIO-RAD, U.S.A.) at 570 nm to calculate the cell viability.

As shown in Table 1, it is confirmed that an inventive extract or compound the present invention did not show cell toxicity.

TABLE 1

Effect of extract and compound isolated from *T. polyphylla* on HL-60 cells.

| Sample | Cell viability (%) | |
|---|---|---|
| | 50 µM | 100 µM |
| *T. polyphylla* extract | 100 | 102 |
| Tiarellic acid | 100 | 102 |

Experimental Example 3

Preparation and Activation of Bone Marrow-Derived Mast Cells (BMMC)

BMMC were obtained from male Balb/c mice and cultured for up to 4 weeks in 50% enriched medium (RPMI containing 2 mM L-glutamine, 25 mM HEPES buffer, 2 mg/ml sodium bicarbonate, 100 units/ml penicillin G, 100 µg/ml streptomycin sulfate, 0.25 µg/ml amphotericin B) supplemented with 10% fetal bovine serum with IL-3 (Sigma I4144, 2 ng/ml) (Murakami M et al., *J. Bio. Chem.*, 39, pp 22653-22656, 1995). 3 weeks after the culture, more than 98% of BMMC was found in the cells as assessed by staining method with toluidine blue.

BMMC were suspended in the enriched medium at the cell density of $1 \times 10^6$ cells/ml, and were then incubated in a humidified 5% $CO_2$ incubator with or without sample in DMSO (final DMSO concentration was less than 0.5%) for 30 min at 37° C. After the stimulation with stem cell factor (SCF, Sigma S9915, 100 ng/ml) for 20 min, the $LTC_4$ release in supernatants was measured by an enzyme immunoassay kit (Cayman Chemical, Ann Arbor, Mich., U.S.A.) according to the manufacturer's instructions. All the experiments were carried out in triplicate and the inhibition of $LTC_4$ release was determined by calculating % reduction of $LTC_4$ release from the control (Lee S H et al., *Biol. Pharm. Bull.*, 27, pp 786-788, 2004).

Experimental Example 4

The Effect of the Extract of *T. polyphylla* and Tiarellic Acid on $LTC_4$ Release As described in Experimental Example 3, the inhibitory effect of the extract of *T. polyphylla* and tiarellic acid on cysteinyl lukotriene release was measured in BMMB using by $LTC_4$-monoclonal antibody ELISA method.

The result demonstrated that the $IC_{50}$ of tiarellic acid was significant but lower than zileuton known as a 5-lipoxygenase inhibitor (See Table 2)

TABLE 2

| sample | $LTC_4$ release inhibition ($IC_{50}$) |
|---|---|
| Extract of *T. polyphylla* | 19.5 µg/ml |
| Tiarellic acid | 2.49 µM |
| zileuton | 0.11 µM |

Experimental Example 5

The Effect of the Extract of *T. polyphylla* and Tiarellic Acid on Airway Hyperresponsiveness (AHR)

24 hours after the final aerosol challenge AHR was measured by using a whole-body plethysmography (OCP3000; Allmedicus, Korea)(Hamelmann E et al., *Am J Respir Crit. Care Med.*, 156, pp 766-775, 1997). Each mouse was placed in a brometric phlethysmographic chamber and challenged with aerosolized PBS, followed by increasing concentrations of aerosolized methacholine (12.5, 25 and 50 mg/ml) for 3 min. Bronchoconstriction was recorded for additional 5 mins at each concentration. The highest Penh value of each sample was obtained during each methacholine challenge, and expressed as a percentage of a basal Penh value in response to control (PBS) challenge.

Figure 2:
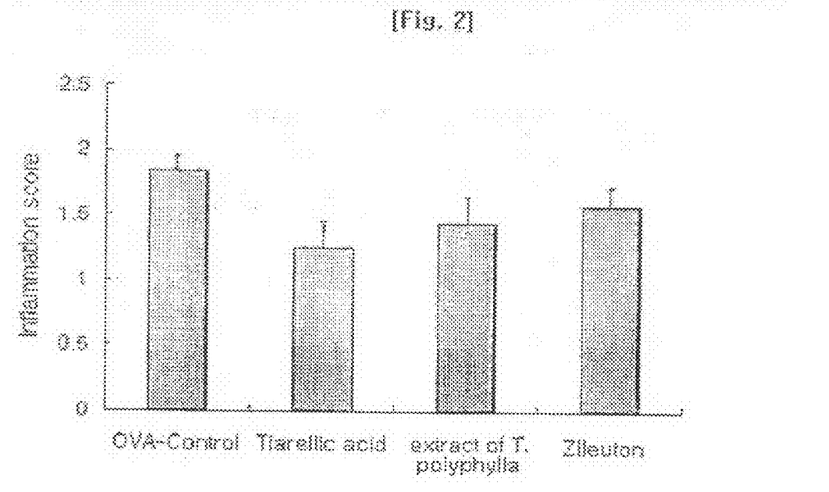
FIG. 2 shows the inhibitory effects of an extract of *T. polyphylla* and tiarellic acid on OVA-induced inflammation in lung tissue.

As shown in Table 3, the Penh value of the OVA-treated group was significantly higher than that of the PBS control group (P<0.05) at any concentration of 5-20 mg/ml of methacholine. In the tiarellic acid+OVA-challenged group, the Penh value was significantly reduced compared with that of the OVA-treated group (P<0.05). A positive control, zileuton developed as an anti-asthmatic drug, showed a decrease of AHR but less than tiarellic acid (See FIG. 2)

TABLE 3

Effect of extract of *T. polyphylla* and tiarellic acid on airway hyperresponsiveness (AHR)

| | Penh value Metacholine (mg/ml) | | | |
|---|---|---|---|---|
| sample | 0 | 5 | 10 | 20 |
| OVA-control | 0.73 ± 0.20 | 1.23 ± 0.48 | 2.19 ± 0.58 | 2.89 ± 0.73 |
| Extrac of *T. polyphylla* | 0.60 ± 0.06 | 1.79 ± 0.47 | 3.25 ± 0.75 | 2.54 ± 0.57* |
| Tiarellic acid (30 mg/ml) | 0.46 ± 0.08 | 0.96 ± 0.45* | 1.54 ± 0.74* | 2.15 ± 0.52* |

TABLE 3-continued

Effect of extract of *T. polyphylla* and tiarellic acid on airway hyperresponsiveness (AHR)

| sample | Penh value Metacholine (mg/ml) | | | |
|---|---|---|---|---|
| | 0 | 5 | 10 | 20 |
| Zileuton (30 mg/ml) | 0.55 ± 0.14 | 1.17 ± 0.59 | 1.97 ± 0.83 | 2.49 ± 0.90 |

*significant difference from OVA treated group, $p < 0.05$

Experimental Example 6
The Effect of Tiarellic Acid on OVA-Specific IgE 48 hours after the last challenge, the mice were sacrificed with an overdose of pentobarbital (Sigma P3761), and a tracheotomy was performed. After ice-cold PBS (0.5 ml) was instilled into the lungs, bronchoalveolar lavage fluid (BALF) was obtained by aspiration three times (total 1.5 ml) via tracheal cannulation. BALF was centrifuged and supernatants were collected and stored at −70° C. before use. The amount of IL-4, IL-5 and IL-13 in BALF was measured by a specific mouse ELISA kit (R&D Systems; Minneapolis, Minn.) according to the manufacturer's instructions. The detection limit of the assays was 250 pg/ml.

Plasma was obtained by cardiac puncture after the tracheotomy. Complementary capture and detection antibody pairs for mouse IgE antibodies were purchased from BD OptEIA (San Diego, Calif.), and the IgE enzyme-linked immunosorbent assay (ELISA) was performed according to the manufacturer's directions. Duplicate samples in plasma were diluted to 1:100. IgE levels in each sample were measured the optical density readings at 450 nm, and OVA-specific IgE concentrations were calculated from a standard curve, which was generated in case recombinant IgE (5-2,000 ng/ml) was used.

As shown in Table 4, the IgE level of tiarellic acid-treated mice was significantly reduced, and zileuton showed similar suppressive effect to tiarellic acid.

TABLE 4

| sample | OVA-specific IgE |
|---|---|
| OVA-control | 26.0 ± 10.9 |
| OVA + tiarellic acid (30 mg/ml)(% inhibition) | 13.3 ± 5.27*(48.8 ± 20.3%) |
| OVA + zileuton (30 mg/ml)(% inhibition) | 14.1 ± 1.0*(45.8 ± 15.3%) |

*significant difference from OVA treated group, $p < 0.05$

Experimental Example 7
The Effect of the Extract of *T. polyphylla* and Tiarellic Acid on Cytokine Levels To determine the effect of extract of *T. polyphylla* and tiarellic acid on the cytokine release in the OVA-induced asthmatic mice, 48 hours after the last challenge, the levels of cytokines (IL-4, IL-5 and IL-13) in BALF were measured by using ELISA method.

As shown in Table 5, the cytokines in the tiarellic acid-treated group were significantly suppressed; 90.5±4.0%, 54.6±23.0% and 43.7±28.2% more decrease in IL-4, IL-5 and in IL-13 ($P<0.05$), respectively than a OVA-challenged group. Zileuton also showed more reduced activity than the control but far less than tiarellic acid. These results demonstrate that tiarellic acid significantly reduced the concentration of IL-4, IL-5 and IL-13 in the BALF of the asthmatic model.

TABLE 5

| sample | IL-4 (pg/ml) | IL-5 (pg/ml) | IL-13 (pg/ml) |
|---|---|---|---|
| OVA-control | 356.1 ± 14.7 | 180.4 ± 17.3 | 145.0 ± 10.9 |
| OVA + extract of *T. polyphylla* (30 mg/ml) (% inhibition) | 294.7 ± 38.2* (18.9%) | 379.5 ± 94.9* (26.8%) | 32.3 ± 9.7** (62.4%) |
| OVA + tiarellic acid (30 mg/ml) (% inhibition) | 33.8 ± 14.3* (90.5%) | 81.9 ± 41.4* (54.6%) | 81.7 ± 40.9* (43.7%) |
| OVA + zileuton (30 mg/ml) (% inhibition) | 289.5 ± 59.0 (18.7%) | 157.8 ± 41.3 (12.5%) | 130.1 ± 16.8 (10.3%) |

*significant difference from OVA-control group, $p < 0.01$
**significant difference from OVA-control group, $p < 0.05$

Experimental Example 8
Effect of the Extract of *T. polyphylla* and Tiarellic Acid on OVA-Induced Inflammation in Lung Tissue The lung tissue was fixed for 24 hours on 10% neutral-buffered formalin. After being embedded in paraffin, the tissues were sliced made into 4-μm thickness sections, and stained with H&E solution (hematoxylin; Sigma MHS-16 and eosin, Sigma HT110-1-32). Subsequently, the stained tissue was mounted and cover-slipped with Dako-mounting medium (Dakocytomation; Denmark Carpinteria Calif.). The degree of cell infiltration in the airway was scored in a double-blind test performed by two independent investigators (Myou S et al., *J. Exp. Med.*, 198, pp 1573-1582, 2003). The peri-bronchiole and peri-vascular inflammation was evaluated by specific standard, i.e., scoring of 0-3, 0, no cells; 1, a few cells; 2, a ring of cells 1 to 5 cell-layer deep; 3, a thick ring of cells more than 5 cell-layer deep. To evaluate the suppressive effect of *T. polyphylla* extract and tiarellic acid on the leukocyte infiltration, the degree of inflammation was scored by quantitative analysis in lung tissues 48 hours after the last challenge (See FIG. 2).

Figure 1:
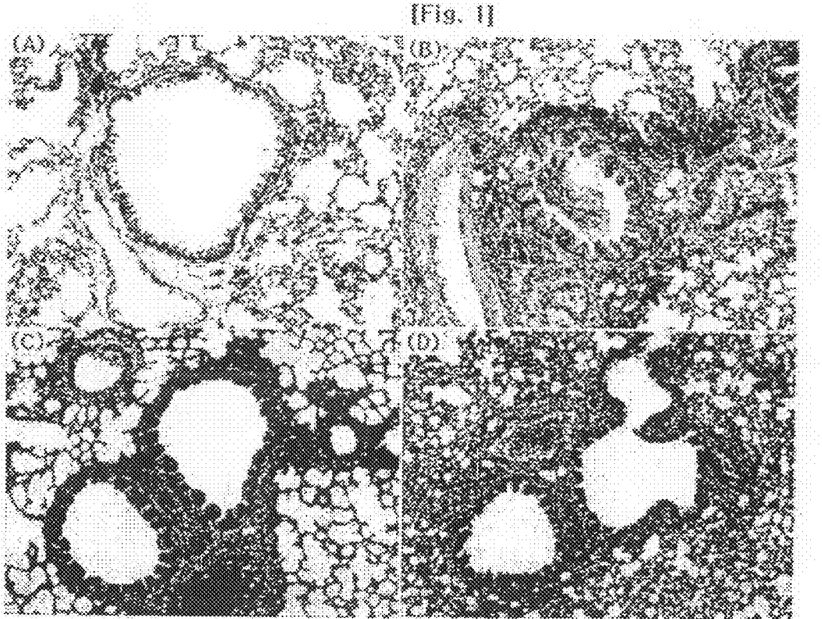
FIG. 1 shows the effects of an extract of *T. polyphylla* and tiarellic acid on lung tissue cell using by the histological examination of bronchoalveolar lavage (A: normal control mice, B: PBS-treated mice, C: *T. polyphylla* extract-treated mice, D: tiarellic acid-treated mice)

As shown in FIG. 1, tiarellic acid showed most potent suppressive effect on the inflammation in the lung tissues of OVA-induced mice and followed by extract of *T. polyphylla* and zileuton. In the H&E staining of lung tissues leukocytes in the OVA-treated mice were greatly infiltrated into the peri-bronchiole and peri-vascular connective tissue from normal mice. In the extract of *T. polyphylla* or tiarellic acid treated mice, the infiltration of eosinophil-rich leukocytes was significantly attenuated compared with the OVA-treated mice.

Experimental Example 9

Effect of the Extract of *T. polyphylla* and Tiarellic Acid on Carageenan-Induced Rat-Paw Edema The inhibiting activity of the extract of *T. polyphylla* and tiarellic acid prepared from the above Examples on the edema formation in ICR rat was determined as follows.

The mice were divided into three groups consisting of 6 rats for each group, i.e., T1 treated with only solvent as a negative control group, T2 treated with 50 mg/kg of the extract of *T. polyphylla*, T3 treated with 50 mg/kg of aspirin respectively. 1 hour after the treatment, 1% carragenan solution was injected into inner rat ankle to induce edema and the thickness of ankle was measured by Vernier's caliper to determine the degree of the edema. The determined thickness was calculated by following Math Fig. 1.

The thickness ratio of ankle(%)=[(maximum thickness of rat paw edema)−(the thickness of pre-treated rat paw edema)/(the thickness of pre-treated rat paw edema)]×100    MathFigure 1

As shown in Table 6, the edema reached to maximum 4 hours after the treatment. Accordingly, it was confirmed that the extract of *T. polyphylla* and tiarellic acid showed potent inhibition effect on rat paw edema.

TABLE 6

| | T1 | T2 | | T3 | |
|---|---|---|---|---|---|
| hr | The thickness ratio of ankle (%) | The thickness ratio of ankle (%) | Inhibition (%) | The thickness ratio of ankle (%) | Inhibition (%) |
| 0 | 100 | — | — | — | — |
| 1 | 119.2 ± 15.6 | 125.1 ± 1.5 | −5.0 ± 1.3 | 139.3 ± 40.6 | −16.8 ± 34.0 |
| 2 | 158.0 ± 9.0 | 146.4 ± 19.4 | 7.3 ± 12.3 | 170.4 ± 34.5 | −7.8 ± 21.8 |
| 3 | 194.9 ± 12.4 | 166.8 ± 18.8 | 14.4 ± 9.7 | 180.6 ± 28.6 | 7.3 ± 14.7 |
| 4 | 205.9 ± 19.0 | 180.6 ± 26.9 | 12.3 ± 13.1 | 196.9 ± 15.4 | 4.3 ± 7.5 |
| 5 | 201.6 ± 5.1 | 193.4 ± 22.4 | 4.1 ± 11.1 | 198.5 ± 12.6 | 1.5 ± 6.3 |

T1: control
T2: 50 mg/kg of the extract of *T. polyphylla*
T3: 50 mg/kg of aspirin Hereinafter, the formulating methods and kinds of excipients will be described, but the present invention is not limited to them. The representative preparation examples were described as follows.

Preparation of Injection
Dried powder of Example 1 or tiarellic acid 100 mg
Sodium metabisulfite 3.0 mg
Methyl paraben 0.8 mg
Propyl paraben 0.1 mg
Distilled water for injection optimum amount
Injection preparation was prepared by dissolving active component, controlling pH to about 7.5 and then filling all the components in 20 ample and sterilizing by conventional injection preparation method.

Preparation of Powder
Dried powder of Example 1 or tiarellic acid 500 mg
Corn Starch 100 mg
Lactose 100 mg
Talc 10 mg
Powder preparation was prepared by mixing above components and filling sealed package.

Preparation of Tablet
Dried powder of Example 1 or tiarellic acid 200 mg
Corn Starch 100 mg
Lactose 100 mg
Magnesium stearate optimum amount
Tablet preparation was prepared by mixing above components and entabletting.

Preparation of Capsule
Dried powder of Example 1 or tiarellic acid 100 mg
Lactose 50 mg
Corn starch 50 mg
Talc 2 mg
Magnesium stearate optimum amount
Tablet preparation was prepared by mixing above components and filling gelatin capsule by conventional gelatin preparation method.

Preparation of Liquid
Dried powder of Example 1 or tiarellic acid 1000 mg
Sugar 20 g
Polysaccharide 20 g
Lemon flavor 20 g
Liquid preparation was prepared by dissolving active component, and then filling all the components in 1000☐ ample and sterilizing by conventional liquid preparation method.

Preparation of Health Food
Dried powder of Example 1 or tiarellic acid 1000 mg
Vitamin mixture optimum amount
Vitamin A acetate 70 mg
Vitamin E 1.0 mg
Vitamin $B_1$ 0.13 mg
Vitamin $B_2$ 0.15 mg
Vitamin $B_6$ 0.5 mg
Vitamin $B_{12}$ 0.2 mg
Vitamin C 10 mg
Biotin 10 mg
Amide nicotinic acid 1.7 mg
Folic acid 50 mg
Calcium pantothenic acid 0.5 mg
Mineral mixture optimum amount
Ferrous sulfate 1.75 mg
Zinc oxide 0.82 mg
Magnesium carbonate 25.3 mg
Monopotassium phosphate 15 mg
Dicalcium phosphate 55 mg
Potassium citrate 90 mg Calcium carbonate 100 mg
Magnesium chloride 24.8 mg The above mentioned vitamin and mineral mixture may be varied in many ways. Such variations are not to be regarded as a departure from the spirit and scope of the present invention.

Preparation of Health Beverage
Dried powder of Example 1 or tiarellic acid 1000 mg
Citric acid 1000 mg
Oligosaccharide 100 g
Apricot concentration 2 g
Taurine 1 g
Distilled water 900☐

Health beverage preparation was prepared by dissolving active component, mixing, stirred at 85° C. for 1 hour, filtered and then filling all the components in 1000☐ ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the extract of T. polyphylla and tiarellic acid isolated therefrom show the inhibitory effect of tiarellic acid against $LTC_4$ release in vitro and the suppressive effect on the IgE level and the cytokine (IL-4, IL-5 and IL-13) production, airway hyperresponsiveness, and leukocyte infiltration in OVA-induced asthmatic mice. Therefore, it can be used as the therapeutics or functional health food for treating and preventing inflammatory, allergic and asthmatic disease.

The invention claimed is:

1. A method for treating asthmatic disease in a mammal suffering from asthmatic disease, wherein the method comprises administering a composition comprising a therapeutically effective amount of a crude extract or organic solvent extract of *Tiarella polyphylla*, or tiarellic acid represented by general formula (I)

to the mammal.

2. A method according to claim 1, wherein the crude extract, organic solvent extract, or tiarellic acid is administered in the form of a functional health food.

* * * * *